United States Patent [19]

Magruder et al.

[11] Patent Number: 5,728,088
[45] Date of Patent: Mar. 17, 1998

[54] OSMOTIC SYSTEM FOR DELIVERY OF FLUID-SENSITIVE SOMATOTROPINS TO BOVINE ANIMALS

[75] Inventors: Judy A. Magruder, Mt. View; James B. Eckenhoff, Los Altos; Richard Cortese, Los Gatos; Jeremy C. Wright, Los Altos; John R. Peery, Stanford, all of Calif.; James B. Pike, St. Louis, Mo.; Urano A. Robinson, St. Louis, Mo.; Jonathan P. Smith, St. Louis, Mo.; Lyle E. Ziemann, St. Louis, Mo.

[73] Assignee: ALZA Corporation, Palo Alto, Calif.

[21] Appl. No.: 269,596

[22] Filed: Jul. 1, 1994

Related U.S. Application Data

[60] Continuation-in-part of Ser. No. 513,361, Apr. 20, 1990, abandoned, which is a division of Ser. No. 283,359, Dec. 13, 1988, Pat. No. 5,034,229.

[51] Int. Cl.[6] .................................................. A61K 9/22
[52] U.S. Cl. ............................... 604/892.1; 604/890.1; 424/422
[58] Field of Search ....................... 604/892.1, 890.1, 604/891.1, 122; 424/473, 484, 486, 422–424, 438, 472

[56] References Cited

U.S. PATENT DOCUMENTS

| | | |
|---|---|---|
| 2,779,241 | 6/1957 | Howard . |
| 3,732,865 | 5/1973 | Higuchi et al. ................... 604/892.1 |
| 3,845,761 | 11/1974 | Zaffaroni . |
| 3,845,770 | 11/1974 | Theeuwes et al. . |
| 3,865,108 | 2/1975 | Hartop . |
| 3,882,233 | 5/1975 | Grant et al. ........................... 514/21 |
| 3,896,819 | 7/1975 | Zaffaroni . |
| 3,916,899 | 11/1975 | Theeuwes et al. . |
| 3,987,790 | 10/1976 | Eckenhoff et al. . |
| 3,995,631 | 12/1976 | Higuchi et al. . |
| 3,995,632 | 12/1976 | Nakano et al. . |
| 4,002,173 | 1/1977 | Manning et al. . |
| 4,063,064 | 12/1977 | Saunders et al. ..................... 219/121 |
| 4,077,407 | 3/1978 | Theeuwes et al. . |
| 4,088,864 | 5/1978 | Theeuwes et al. ..................... 219/121 |
| 4,111,202 | 9/1978 | Theeuwes et al. . |
| 4,111,203 | 9/1978 | Theeuwes . |
| 4,160,020 | 7/1979 | Ayer et al. . |
| 4,179,337 | 12/1979 | Davis et al. . |
| 4,200,098 | 4/1980 | Ayer et al. . |
| 4,203,439 | 5/1980 | Theeuwes . |
| 4,203,440 | 5/1980 | Theeuwes . |
| 4,207,893 | 6/1980 | Michaels . |
| 4,235,236 | 11/1980 | Theeuwes . |
| 4,285,987 | 8/1981 | Ayer et al. ............................... 427/3 |
| 4,309,996 | 1/1982 | Theeuwes . |
| 4,320,759 | 3/1982 | Theeuwes . |
| 4,327,725 | 5/1982 | Cortese et al. . |
| 4,350,271 | 9/1982 | Eckenhoff et al. ..................... 222/386 |

(List continued on next page.)

Primary Examiner—Michael Powell Buiz
Assistant Examiner—At Nguyen
Attorney, Agent, or Firm—Pauline Ann Clarke; John A. Dhuey; Steven F. Stone

[57] ABSTRACT

A delivery system is disclosed for delivering a fluid-sensitive beneficial agent such as a somatotropin, or an analogue or derivative thereof, to an animal such as a bovine. The delivery system comprises a wall that surrounds an internal compartment, said wall comprising a first wall section that limits the passage of fluid into the system and a second wall section that permits the passage of fluid into the system. The wall may further comprise an end cap which may include means for adapting the end cap for ultrasonic welding to the first wall section and means for maintaining the beneficial agent in contact with exit means. The compartment comprises a beneficial agent and an expandable means. The delivery system comprises exit means for delivering the beneficial agent to the animal. The exit means may include means for compensating for slight variations in the efflux rate of the beneficial agent and means for maintaining for a sufficient velocity or efflux rate of beneficial agent outward from the device while minimizing diffusion of fluids from the external environment back into the device.

18 Claims, 6 Drawing Sheets

U.S. PATENT DOCUMENTS

| | | | |
|---|---|---|---|
| 4,475,916 | 10/1984 | Himmelstein | 424/424 |
| 4,526,938 | 7/1985 | Churchill et al. | 525/415 |
| 4,599,229 | 7/1986 | Maccecchini | |
| 4,612,008 | 9/1986 | Wong et al. | |
| 4,612,186 | 9/1986 | Eckenhoff et al. | |
| 4,643,731 | 2/1987 | Ekcenhoff | |
| 4,652,630 | 3/1987 | Bentle et al. | 530/420.4 |
| 4,692,336 | 9/1987 | Eckenhoff et al. | 424/468 |
| 4,717,566 | 1/1988 | Eckenhoff et al. | 424/438 |
| 4,723,958 | 2/1988 | Pope et al. | 604/890.1 |
| 4,756,604 | 7/1988 | Nakatsuka et al. | 350/331 R |
| 4,765,980 | 8/1988 | Deprince et al. | 424/108 |
| 4,781,714 | 11/1988 | Eckenhoff et al. | |
| 4,855,141 | 8/1989 | Eckenhoff et al. | 424/423 |
| 4,957,494 | 9/1990 | Wong et al. | 604/892.1 |
| 4,959,218 | 9/1990 | Eckenhoff et al. | 424/473 |
| 4,960,416 | 10/1990 | Stephens et al. | 604/892.1 |
| 4,963,141 | 10/1990 | Eckenhoff | 604/892.1 |
| 4,969,884 | 11/1990 | Yum | 604/892.1 |
| 4,976,966 | 12/1990 | Theeuwes et al. | 424/473 |
| 5,023,088 | 6/1991 | Wong et al. | 424/473 |
| 5,030,216 | 7/1991 | Theeuwes et al. | 604/892.1 |
| 5,037,420 | 8/1991 | Magruder et al. | 604/892.1 |
| 5,045,082 | 9/1991 | Ayer et al. | 604/892.1 |
| 5,057,321 | 10/1991 | Edgren et al. | 424/413 |
| 5,137,727 | 8/1992 | Eckenhoff | 424/422 |
| 5,209,746 | 5/1993 | Balaban et al. | 604/892.1 |
| 5,221,278 | 6/1993 | Linkwita et al. | 604/890.1 |
| 5,223,265 | 6/1993 | Wong | 424/473 |
| 5,308,348 | 5/1994 | Balaban et al. | 604/892.1 |
| 5,324,518 | 6/1994 | Orth et al. | 424/423 |

OSMOTIC SYSTEM FOR DELIVERY OF FLUID-SENSITIVE SOMATOTROPINS TO BOVINE ANIMALS

CROSS-REFERENCE TO RELATED APPLICATIONS

This application is a continuation-in-part of U.S. Ser. No. 07/513,361, now abandoned; filed Apr. 20, 1990, which is a division of U.S. Ser. No. 07/283,359, filed Dec. 13, 1988, now U.S. Pat. No. 5,034,229, which applications are incorporated herein by reference and benefit is claimed of their filing dates.

This application is also related to U.S. Ser. Nos. 512,301, filed Apr. 20, 1990, now U.S. Pat. No. 5,174,999; 513,327, filed Apr. 20, 1990, now U.S. Pat. No. 5,057,318; 513,328, filed Apr. 20, 1990, now U.S. Pat. No. 5,037,420; 513,330, filed Apr. 20, 1990, now U.S. Pat. No. 5,110,596; 513,363, filed Apr. 20, 1990, now U.S. Pat. No. 5,135,523; and 513,528, filed Apr. 23, 1990, now U.S. Pat. No. 5,059,423; all of which are divisions of U.S. Ser. No. 283,359 (above); 681,848, filed Apr. 8, 1991, now abandoned, which is a continuation of U.S. Ser. No. 513,328 (above); 789,241, now U.S. Pat. No. 5,320,616; filed Nov. 7, 1991, which is a continuation of U.S. Ser. No. 513,369, filed Apr. 20, 1990, now abandoned; and 203,967, filed Mar. 1, 1994, which is a continuation of 789,241 (above).

All of the above applications are assigned to ALZA Corporation, Palo Alto, Calif.

FIELD OF THE INVENTION

This invention pertains to both a novel and to an unobvious delivery system. Particularly, the invention relates to a delivery system that operates by osmosis and more particularly, the invention relates to a device that protects and administers a fluid-sensitive beneficial agent to a fluid environment.

BACKGROUND OF THE INVENTION

Delivery systems for administering a beneficial agent to a biological, fluid environment of use are known to the prior art. See, for example, U.S. Pat. Nos. 3,845,770; U.S. Pat. No. 3,916,899; 3,995,632; 4,111,202; 4,111,203; 4,203,439; 4,327,725; and 4,612,008.

The delivery devices described in the above patents operate successfully for their intended use and they can deliver many beneficial agents for their intended effects. Now, it has been observed that their use can be limited because they lack the necessary elements to deliver beneficial agents that are sensitive to fluids and to fluids containing biological gases. Their use may be limited because beneficial agents that are sensitive to such aqueous-biological fluids or to other fluids external to the delivery device may be adversely affected by fluids that enter the device and contact the beneficial agents during operation of the device. Examples of such fluid-sensitive agents include proteins, peptides, and hormones. Moreover, the prior art devices lack the necessary means for their use as implant devices for dispensing such sensitive agents to a biological fluid-rich environment of use.

It will be appreciated by those versed in the dispensing arts that if a delivery system is provided for administering at a controlled rate and for protecting a beneficial agent that is sensitive to aqueous and biological fluids, and which delivery system possesses the kinetic ability to deliver the protected beneficial agent in effective amounts over time, such a delivery system would have a positive value and represent an advancement in the dispensing arts. Likewise, it will be self-evident to those versed in the implant art that a pressing need exists for an implant that is essentially free of the tribulation associated with the prior art and that, if such an implantable delivery system is provided, it would have a practical application in the fields of human and veterinary medicine and in the breeding and management of farm animals.

SUMMARY OF THE INVENTION

The present invention is directed to a fluid-imbibing delivery device or dispenser for storing and protecting a fluid-sensitive beneficial agent and for dispensing the beneficial agent to a fluid environment of use for a prolonged period of time. The device comprises a housing enclosing an internal compartment, the housing having a first wall section and a second wall section and, optionally, an end cap, the first wall section substantially restricting the passage of fluid into the delivery device, i.e., it is substantially fluid-impermeable, and the second wall section permitting the passage of fluid into the delivery device, i.e., it is fluid-permeable, in at least a portion. The device further comprises a beneficial agent in that portion of the internal compartment defined by the first wall section, expandable means for pushing the beneficial agent from the delivery device in that portion of the internal compartment defined by the second wall section, exit means in the first wall section or in the end cap, if an end cap is present, and, optionally, a partition layer, including a cantilevered piston member, between the beneficial agent and the expandable means, the partition layer being substantially impermeable to fluid. The exit means may include means for maintaining sufficient efflux or outward velocity of the beneficial agent from that portion defined first wall section. The device further optionally comprises forming the portion containing the beneficial agent of a material that reduces the adherence of the beneficial agent thereto. The device further optionally comprises a buttress to strengthen the joint between the first and second wall sections while smoothing the transition between the same.

One class of fluid-sensitive agents that are presently preferred for delivery from the devices of the present invention are growth factors, including bovine somatotropin and analogues and derivatives thereof. The devices of the present invention provide a means for delivering an effective amount of a beneficial agent for causing increased productivity, such as, in the case of the somatotropins, a higher feed conversion efficiency, improved carcass quality, higher than normal rate of animal weight gain, and increased milk production.

BRIEF DESCRIPTION OF THE DRAWINGS

In the drawing figures, which are not drawn to scale, but are set forth to illustrate various embodiments of the invention, the drawing figures are as follows.

DETAILED DESCRIPTION OF THE INVENTION

Figure 1:
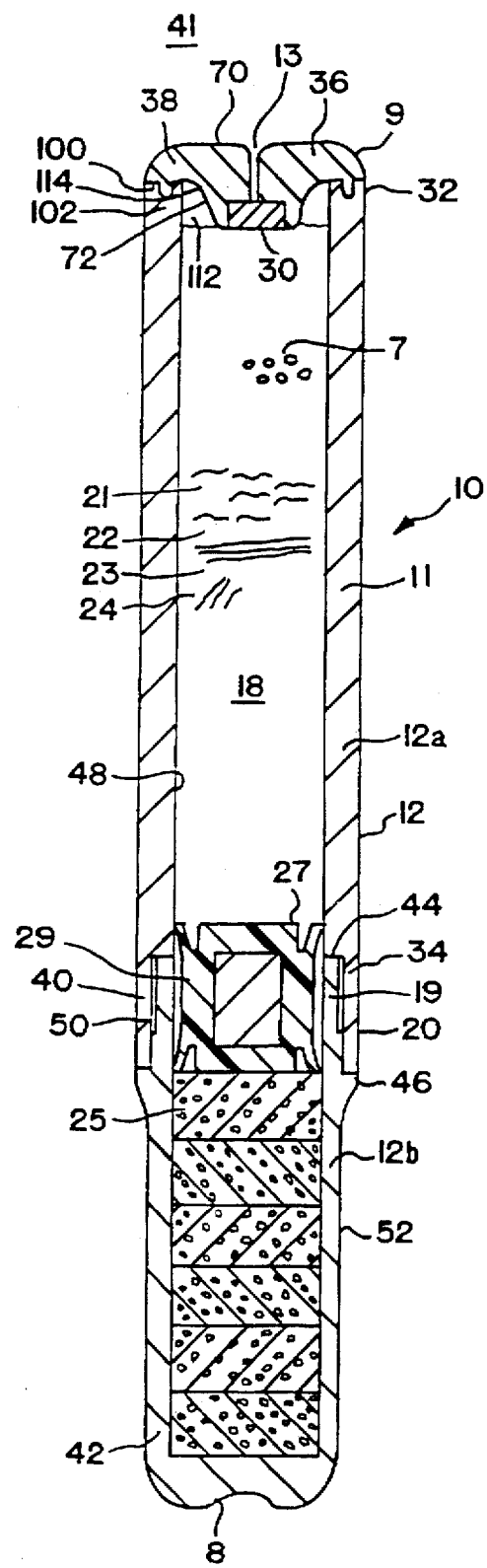
FIG. 1 is a cross-sectional view of one embodiment of the delivery device of the invention, illustrating one structural embodiment of the delivery system comprising a first walled section and a second walled section.

In the following discussion, like reference numerals refer to like elements in the figures.

FIG. 1 depicts in opened view one embodiment of the delivery device according to the present invention. Delivery system 10 of FIG. 1 comprises a housing 11 formed of a wall 12, which wall 12 comprises a first wall section 12a and a second wall section 12b. Wall 12, comprising first wall section 12a and second wall section 12b, surrounds and defines an internal compartment 18. Delivery system 10 has at least one exit passageway 13 for delivering a beneficial agent 7 formulation from delivery system 10. Optionally, the exit passageway can be occluded with a material like that in seal 30, discussed below, that gets discharged, leaches or erodes during the time of use. In FIG, 1, delivery system 10 comprises a dome-shaped rear end 8 and a flattened lead end 9. In embodiments not shown, delivery system 10 can be manufactured with a pair of rounded or flat ends 8 and 9. The term "lead end", as used herein, generally denotes the end from which beneficial agent 7 is released from the system. In use, either the lead end or the rear end may be implanted first.

Wall section 12a may be in the form of a tubular member having a first and a second open ends 32 and 34, respectively. In this particular embodiment, an enclosure means 36 is positioned on first wall section 12a at its end lead 9. In this particular embodiment, the enclosure means is in the form of an end cap 38. The wall section 12a and end cap 38 together form passageway 13, seal 30 and surround that portion of internal compartment 18 that contains a beneficial agent 7 formulation.

Referring now to FIG. 1, wall section 12b has a first or open end 40 and a second or enclosed end 42, the enclosed end at end 8 and the open end distant therefrom. Open end 40 defines and forms receiving means 19. Receiving means 19, having a first buttress 44 and second buttress 46, is received within enclosing means 20 of first wall section 12a. First buttress 44 can be formed by providing the enclosing means 20 of the first wall section 12a with a first interior surface portion 48 having a first inner or bore diameter and a second interior surface portion 50 having a second inner or bore diameter, so that the internal buttress or interior annular ledge 44 is formed or defined where the first and second interior surface portions of wall section 12a meet.

Formed on the outer surface 52 of the wall section 12b is the second buttress 46. Second buttress 46 is positioned to abut with the second open end 34 of the first wall section 12a when the enclosing means 20 of the wall section 12a abuts with the first buttress 44. As a result, the second buttress 46 in combination with the first buttress 44 forms a double butt joint to mate the wall sections 12a and 12b for a strong joint while minimizing the external discontinuities or surface friction of the implant device and providing a smooth transition between the first and second wall sections. In this particular embodiment, the portion of the second wall section 12b inserted within the first wall section 12a has the same thickness as that portion outside the first wall section. In addition, as a result of this construction, the inside surface of the first and second wall sections facilitates the travel of the piston along the formed smooth continuous interior surface.

Figure 5:
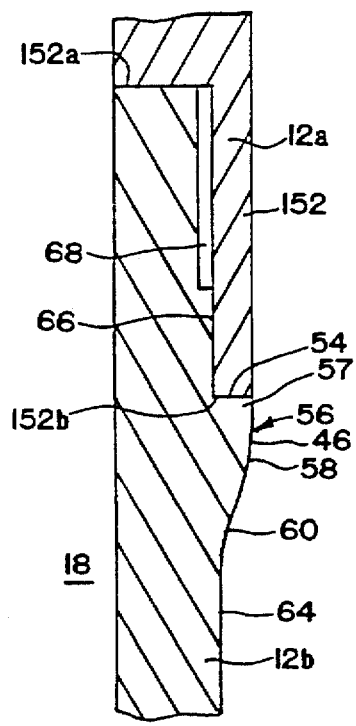
FIG. 5 is an enlarged fragmented cross-sectional view of the joint between the first and second wall sections of FIG. 1.

As best shown in FIG. 5, the buttress 46 includes a buttress engaging surface 54 for abutting with the first wall section 12a and an exterior or contoured surface 56 to smooth the transition from the exterior surface of the first wall section 12a to the exterior surface of the second wall section 12b. In the illustrated embodiment, contoured surface 56 when viewed in cross-section, has a generally s-shape. The contoured surface 56 includes a non-tapered annular portion 57, an annular convex portion 58 and a concave annular portion 60. In one particular embodiment, the contoured annular surface 56 includes a non-tapered annular portion 57 which extends distally away from the engaging surface 54 and towards the end 8 a short distance, for example about 0.010 inches, generally parallel to the inside surface of the second wall section and has an outer diameter substantially equal to that of the first wall section 12a. This generally annular portion 57 terminates in and is integral with the convex annular portion 58, having a slope with a radius of about 0.115 inches. The convex portion 58 connects and is integral with concave annular portion 60, having a concave slope with a radius of about 0.300 inches. The concave annular portion 60 terminates in and connects with the outer portion 64 of the second wall section 12b having a different diameter, in this example smaller, than outer diameter of the first wall section 12a. As a result, the buttress 46 extends smoothly radially outward from the exterior surface of the second wall section to the exterior surface diameter of the first wall section, smoothing the transition between sections of the device having different outer diameters.

Wall section 12b surrounds that portion of internal compartment area 18 that contains a means 25 for expanding and for occupying space in compartment 18 for delivery of a beneficial agent formulation from delivery system 10. The thickness and the surface area of the second wall section 12b contribute to the rate of passage of fluid through the membrane second wall section. In the preferred embodiment the second wall section or membrane cap 12b is about 1.442 inches long, with an inner diameter of about 0.288 inches. The second wall section 12b has an outer diameter of about 0.365 inches at the receiving end 19 and about 0.378 inches at the portion not inserted within first wall section 12a. A membrane cap of substantially these dimensions provides a desired fluid flow rate into the second wall section of about 10–15 mg $H_2O$/day and more particularly about 12–14 mg H₂O/day. The two wall sections, sections 12a and 12b, at receiving means 19 and enclosing means 20 are close in size. There is clearance or tolerance in size to allow enclosing means 20 of wall section 12a a sliding movement over the receiving means 19 of wall section 12b and provide a small gap, preferably between 0.002–0.006 inches, between the wall sections so that a cyanoacrylate adhesive with good gap filling characteristics will wick to form a bond between 19 and 20. In one preferred embodiment, the outside diameter of the second wall section 12b is about 0.362 inches, and the inside diameter of the first wall section is about 0.365, providing a space of about 0.003 inches. Wall section 12a and wall section 12b can be telescoped completely until halted by buttresses 44 or 46 into a closed and continuous internal walled position. In the illustrated embodiment, optionally, a plurality of longitudinal ribs 66 formed upon the outer surface of the second wall section on the lead end or side of the engaging wall 54, space apart the first and second wall sections to define and form adhesive receiving cavities 68 between the first and second wall sections and in between the longitudinal ridges. Optionally, the wall sections 12a and 12b can be held together by heat fusion, by an adhesive, or the like. Preferably the adhesive is a cyanoacrylate adhesive having a low-enough viscosity to wick into the joint and form a secure bond. A cyanoacrylate adhesive having the same qualities and characteristics as that sold by Permabond of National Starch and Chemical Company under the brand name Permabond USP Grade 701 Adhesive is sufficient for the purposes of this invention. Buttresses 44 and 46 ensure that the juncture of 12a and 12b are smoothly and precisely joined in mated contact without discontinuities which would facilitate encapsulation of device 10.

Figure 3:
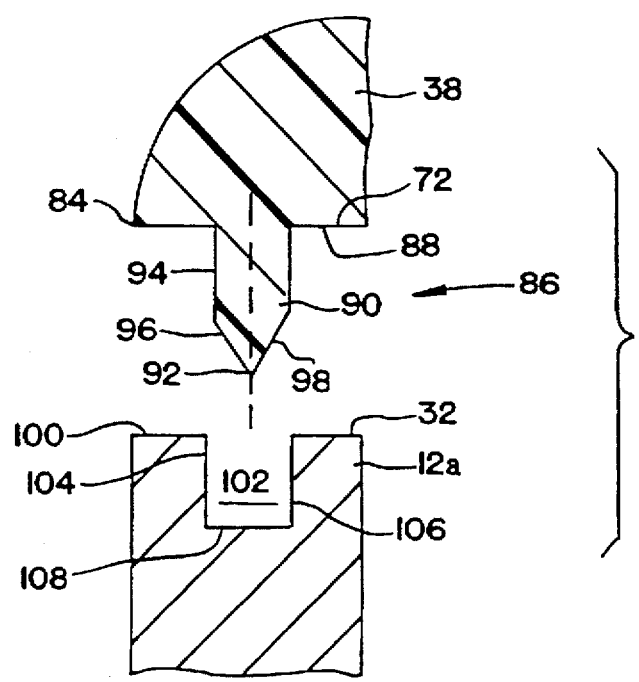
FIG. 3 is an enlarged fragmented cross-sectional view of the tenon and mortise embodiment of the mating end cap of FIG. 2.

Referring again to now to FIG. 1, there is shown, as discussed in more detail with regards to FIG. 3, an embodiment of the mating end cap 38, adapting the end cap for ultrasonic welding to the first wall section 12a; and maintaining the exit passageway 13 in contact with the beneficial agent 7, while minimizing the dilution of the beneficial agent by adjacent body fluids present at the environment of use 41.

The end cap 38 is designed with specific features applicable to slow release implants osmotically driven being one specific type, that required pressure drop for the operation of the implant. The cap is specifically beneficial when delivering fluid sensitive materials and protects the material to be delivered before and after activation of the device. The engineered exit port provides for a specific superficial formulation flow rate to eliminate dilution of the formulation by external fluids and maintains a required pressure drop for the operation of the implant. The engineered internal seal that provides point of use readiness without having to reopen the device also provides for a long term stability seal, protects formulation at start-up and has an engineered consistent rupture pressure for consistent startup. Designed headspace and internal configuration minimizes internal pressure from thermal expansion of formulations. An exit port maintains contact with the formulation through all phases of the pump operation. Ultrasonic weld for application of the cap that is designed for automated application protection of formulations during the welding process, and gives a biocompatible joint seam as a result of a melt sink designed into the weld configuration.

As best shown in FIG. 1, end cap 38 includes a first end cap side 70, a second end cap side 72 and an exit passageway 13 extending from the external environment 41 into internal chamber 18. Exit passageway 13 is designed for an adequate formulation flow rate, driven by driving member 25 and a partition member 27 including piston 29 to prevent dilution of the formulation in chamber 18 by the inflow of fluids from external environment 41. Exit passageway 13 also maintains the pressure drop for a given rate of release of the formulation from device 10. Exit passageway 13 is preferably designed so that the rate of outflow of formulation exceeds the rate at which fluids from the external environment diffuse inwards.

Figure 2:
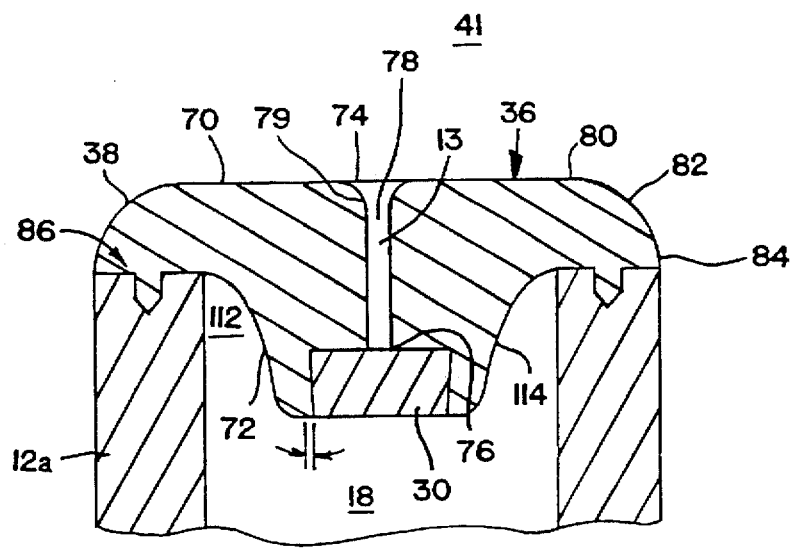
FIG. 2 is an enlarged fragmented cross-sectional view of the mating end cap of FIG. 1.

Referring now to FIG. 2, exit passageway 13 further includes first side 70 defining a first concentric exit aperture 74, in the preferred embodiment having a diameter of about 0.075 inches. Second side 72 defines a second exit aperture 76, in the preferred embodiment having a second diameter of about 0.017 inches. Concentric communicating passageway 78, having the same diameter as the second exit aperture, fluidly connects the first exit aperture 74 with the second exit aperture 76 over a distance of about 0.100 inches to provide a means for the beneficial agent 7 to pass from the second side of the end cap to the first side of the end cap and out to the external environment 41. The diameter of the exit passageway 76 determines the velocity of the efflux or outward flow of the beneficial agent 7 from the portion of the internal compartment comprised of the first wall section 12a in the preferred embodiment, a passageway diameter of 0.017 inches is sufficient to generate a sufficient outward velocity of the beneficial agent therefrom. The length of the exit passageway provides a means for compensating for slight variations in the efflux or outward flow rate of the beneficial agent. In one embodiment, a passageway length of 0.100 inches was sufficient. First side 70 includes an external face 80, the external face generally defining a plane substantially perpendicular to the longitudinal axis of the end cap 38. The communicating passageway 78 has a generally frustro-conically shaped contoured interior annular surface portion 79, smoothly joining the larger diametered first exit aperture 74 with smaller diametered communicating passageway 78 and second exit aperture 74. In one embodiment, the surface has a radius of about 0.028 inches, with a center 0.028 inches from the external face 80 and 0.028 inches from the surface of the communicating passageway 78.

Along its outer edge, the external face 80 joins with an annular concentric rounded portion 82 for rounding off the edges of the devise. In this particular embodiment, the annualar rounded portion 82 is defined by a radius of about 0.066 inches, with a center about 0.066 inches radially inward from the outermost edge 84 and about 0.066 inches inward from the end face 80.

As best shown in FIG. 3, second side 72 of end cap 38 also includes a mating portion 86 for engaging or mating with the first wall section 12a, adapted for ultrasonic welding. The mating portion 86 includes an annular mating surface 88 on the second side 72 for engaging with the first wall section 12a, and a tenon 90 extending outward therefrom towards the first wall section 12a. In one particular embodiment, the annular tenon 90 has an annular thickness of about 0.018 inches, and is formed about 0.018 inches from the outermost edge 84 and extends outward from the mating surface 88 to terminate in a apex 92. The tenon 90 includes an first portion 94 that extends outward from the annular mating surface 88 a distance of about 0.026 inches. Apex 92 includes a pair of angular oblique faces 96 and 98 which are angled at about 28° from the vertical, i.e., a plane generally parallel to the longitudinal axis of the end cap 38.

As earlier described, first wall section 12a includes first open end 32. The open end 32 has an engaging surface portion 100 for engaging with the end cap 38. This surface or open end 100 defines a mortise 102 for receipt of the tenon 90 extending outward from the mating surface 88 of the end cap 38. In one particular embodiment, the mortise is defined by a first mortise wall 104, a second mortise wall 106 and a mortise bottom wall 108, the first and second walls 104 and 106 generally parallel to the longitudinal axis of the first wall section 12a and spaced apart about a distance of 0.030 inches. The mortise bottom surface 108 connecting the first and second side walls 104 and 106 at a depth of about 0.026 inches from the engaging surface 100 of the first wall section 12a.

Referring again to FIG. 1, it can be seen that end cap 38 is adapted with an inward extending portion 114 which defines a headspace 112 between wall 12a and end cap 38, such that when the end cap is engaged with wall 12a, defining chamber 18 which is filled with beneficial agent formulation 7, any resulting volume in chamber 18 which does not contain formulation is confined to the headspace. In this way, regardless of the orientation of device 10, beneficial agent formulation is in contact with seal 30 or with exit passageway 13 and entrance of fluid into chamber 18 from external environment 41 is inhibited.

Figure 4:
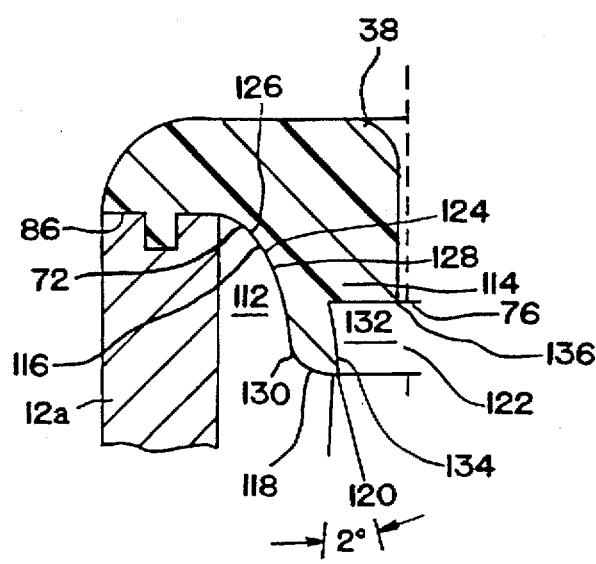
FIG. 4 is an enlarged fragmented cross-sectional view of the extending portion of the mating end cap and first wall section of FIG. 1 which maintains the exit passageway in contact with the beneficial agent.

As best shown in FIG. 4, second side 72 of end cap 38 also includes an extension 114 for sealing the exit passageway 13 and maintaining the exit passageway in contact with the beneficial agent 7 disposed within a portion of the internal chamber 18. The extension 114 includes a generally cylindrical portion 116, extending outward and integral with the annular mating portion 86 such that when the end cap 38 is mating with the first wall section 12a, the annular cavity 112 is defined therebetween to accumulate an air volume inserted or present in the internal compartment 18 to allow for differential expansion of beneficial agent and plastic within the interior chamber 18. The extension portion 114 at its terminal portion 118 includes an end cap apex 120. Apex 120 includes or defines therein a depot 122 for receipt of a sealant. A sloping contoured surface 124 extends and connects the annular mating surface 86 with the depot 122. In one embodiment, the sloping surface 124 is generally s-shaped in cross-section and includes a first concave annular portion 126, a second concave annular portion 128, and a convex annular portion 130 forming a generally s-shaped surface in cross-section. In one preferred embodiment, the first concave annular portion 126 has a slope generally defined by a radius of about 0.029 inches from a center 0.125 inches radially outward from the central longitudinal axis and 0.083 inches along the central longitudinal axis from the apex 120 on second side 72. The second concave annular portion 128, integral with and extending radially inward from the first concave annular portion 126, joins with the convex annular portion 130, and has a slope generally defined by a radius of about 0.125 inches from a center at 0.200 inches radially outward from the central longitudinal axis and 0.026 inches along the central longitudinal axis from the annular 120 on the second side 72. The convex apex portion 130 has a slope generally defined by a radius of about 0.026 inches from a center 0.026 inches radially outward from the central longitudinal axis of the end cap 38 and the apex 120 on the second side 72. In addition FIG. 4 illustrates that after welding of the end cap 38 to the first wall section 12a, the outer surface of the tenon 90 may be altered by the welding procedure to generally assume a shape similar to that of the mortise 102.

Depot 122 is comprised of the apex 120 defining a depot bore 132, for receipt of the sealant 30, the depot bore in fluid communication with the interior chamber 18 and the exit passageway 13. In the preferred embodiment, the depot bore 132 is defined by a generally cylindrical first or bore side interior surface 134 and a generally planar bottom surface 136, the bore having a diameter of about 0.100 inches and a depth of about 0.050 inches. The bore side surface 134 slopes generally inward towards the longitudinal axis of the end cap 38 as the surface extends from the end proximal to the second exit aperture 76 to the end distant from the exit aperture at an oblique angle. In the preferred embodiment, the oblique angle is about 2° from the axis parallel to the central longitudinal axis of the end cap 38.

In the handling and operation of the device, the relationship between headspace 112, depot 122 and exit passageway 13 plays a significant role. Headspace 112 permits contraction and expansion of the formulation 7 in device 10 during shipping and handling and also provides for the buildup of pressure in device 10 after implantation into an animal. Headspace 112 insures that any air left in the formulation is not in the formulation where it can form a bubble adjacent to exit passageway 13 but is confined to head space 112. If a bubble were permitted to form adjacent exit passageway 13, then when pressure built up sufficient to expel the plug in depot 122, an inflow of fluid from the external environment could dilute the formulation and the rate of delivery of formulation from device 10. In filling the device, heat treatment after filling assists in "setting" the formulation, locking the air bubble into place in headspace 112 where it will not affect initial operation of device 10.

Figure 6:
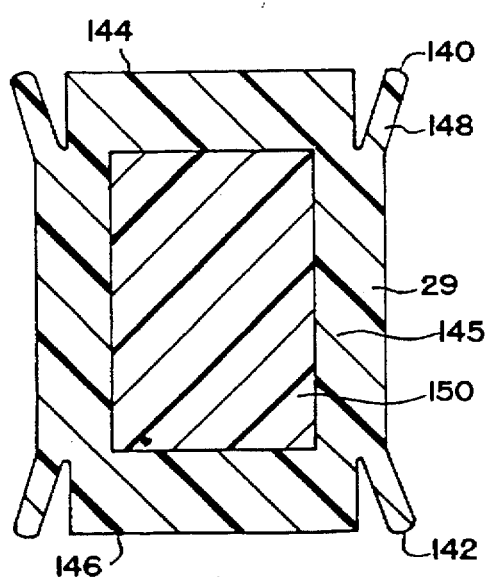
FIG. 6 is an enlarged cross-sectional view of the piston member of FIG. 1.

FIG. 6 illustrates in greater detail piston 29 of FIG. 1. Piston 29 is an elastomeric piston generally cylindrical in shape which incorporates first and second deformable seals 140 and 142. Piston 29 provides a high interference seal with minimum lateral force applied to the device wall which would impede longitudinal travel of the piston. The deformable seals 140 and 142 compensate for any irregularities in the internal wall of device 10 to provide an effective seal. The piston material, in one preferred embodiment, can be formed of any of four grades of Santoprene® 271 material, the most preferred grade being 271-55.

Figure 7:
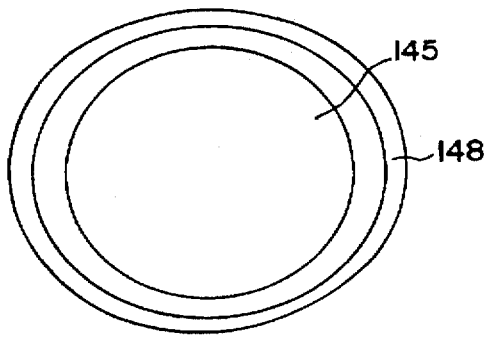
FIG. 7 is an enlarged top elevational view of the piston member of FIG. 1.

In one embodiment, the piston 29 includes a cylindrical body portion 145 positioned within the first wall section 12a. The piston 29 includes the cylindrical first or central body member 145 with first and second piston ends 144 and 146 respectively. The deformable seals 140 or 142 are formed at first and second piston ends 144 and 146 respectively. In one particular embodiment, the deformable seals 140 and 142 include a flared, conical skirt member or section 148. As best shown in FIGS. 6 and 7, the skirt 148 extends radially outward from the central body member 145 to terminate at a position spaced apart therefrom. Referring again to FIG. 6, a metal location detection member 150 is formed within the central cylindrical body member 145. The skirt member 148, extends radially outward a distance of about 0.016 inches from the respective piston end surface to extend longitudinally a distance of about 0.079 inches at an oblique angle of about 15 degrees from the plane generally defined by the surface of the central body member 145. As a result, the distal ends of the piston 29 are biased radially outward when articulating within the inner diameter of the first wall section 12a. The thickness of the skirt enables the skirt to provide sufficient wiping pressure to the inside surface of the first wall section without invoking such pressure as to cause the skirt to fold over.

Referring again to FIG. 5, first wall section 12a at its end distant from lead end 9 defines and forms an open end having a circumference for forming a lap joint 152 with wall section 12b. Second wall section 12b defines rear end 8 and it surrounds that portion of internal compartment 18 which initially contains an expandable driving means, here illustrated by expandable driving members 25a–f. Second wall section 12b at its end distant from rear end 8 defines and forms an open end having a circumference for forming lap joint 152. Second wall section 12b is adapted with buttress 56 for strength and precision of manufacture. Preferably the buttress is shaped to provide a smooth surface transition between wall sections 12a and 12b to minimize irritation leading to encapsulation.

Lap joint 152 includes, in the illustrated embodiment, lap joints 152a and 152b, reciprocally received one within the other for mating engagement when the two edges are assembled together. The lap joints 152a and 152b are of such a design as to provide a strong mechanically and hydrostatically intact seal when they are bonded together with an adhesive, such as a pressure-sensitive contact adhesive, a moisture-curing adhesive, an ultraviolet-curing adhesive or the like. While FIG. I shows the two wall sections assembled with the lap joint 152a of first wall section 12a enclosing the outside of the lap joint 152b of second wall section 12b, this arrangement is not critical and may be reversed. However, the illustrated embodiment is preferred since it provides additional restraint on the second wall section or membrane cup 12b pulling away from the lap joint. In addition, if the material used in the formation of the wall section surrounding the osmotic driving member, for example wall section 12b, is not as strong as the material used in the formation of the portion surrounding the beneficial agent 7, for example first wall section 12a, then the weaker material is preferably positioned or disposed to the inside or inserted within the stronger material. For example, if cellulose acetate butyrate is used for the portion surrounding the osmotic driving member and polypropylene is used to surround the beneficial agent 7, then the cellulose acetate butyrate wall is preferably on the inside of the polypropylene wall.

In one embodiment of delivery device 10 as illustrated of FIG. 1, the system is manufactured as an implant comprising a body length of about 8.7 cm, a diameter of the first wall section of about 10.5 mm, a diameter of the second wall section of about 9 to 10.5 mm, a beneficial agent 7 formulation occupying a length of about 45 mm, an initial total length of about 26.54 mm, occupied by the expandable driving members, and an exit passageway of 2.5–2.6 mm in length and having a diameter of 0.017 inches. This diameter has been found effective to restrict flow of materials inwardly from the environment of use which the device is in use. In a presently preferred embodiment, the exit passageway 13 and depot 122 are occluded with a material such as wax that gets discharged, leaches or erodes when placed in the organic environment of use. The implant can be implanted into the peritoneal cavity using an implanter.

Generally, an implanter comprises a tubular member with a central longitudinal axial bore, a pointed, elongated, annular concavely beveled implanting end and an implant-charging end. The implanting end and the charging end communicate through a bore. A plunger adapted to be removably inserted in the bore is designed for slidable movement therein for applying the necessary force for implanting the implant. Alternatively, the implant can be surgically or subcutaneously implanted in the peritoneal cavity.

Referring again to FIG. 1, first wall section 12a comprises a composition that is substantially impermeable to the exchange of fluid, beneficial agent 7 and other ingredients contained in delivery system 10. Wall section 12a, in a presently preferred manufacture, is substantially impermeable to the ingress/loss of an external/internal fluid to serve as a means for substantially protecting a beneficial agent 7 that is sensitive to exterior fluid present in the environment of use. Wall section 12a substantially restricts and prevents fluid from passing through wall 12a and entering into compartment 18 in the region containing a beneficial agent formulation. In one particular embodiment, when used in conjunction with bovine growth factors, including bovine somatotropin, wall section 12a may be formed of a material which provides a reduced adherence of the beneficial agent 7 to the wall 12a. For example, the use of polypropylene in the construction of wall 12a will reduce the adherence of bovine somatotropin to the surface of wall 12a.

In the preferred embodiment, wall section 12a is formed of polypropylene because of its excellent low permeability to water and because of its low surface tension which facilitates non-adhesion of beneficial agent 7 to the internal surface as compared with other materials such as polycarbonates, which empirically appeared to result in increased bearding on the respective wall surface/beneficial agent interface, especially when the beneficial agent included bovine somatotropin. Preparing polypropylene for bonding preferably includes preparing the surface thereof to increase the likelihood of an effective seal. Those skilled in the art will recognize that this may be performed by various methods, a non-inclusive list includes, for example, by priming with a chemical primer, abrading or knurling the surface, treatment with plasma and the like.

Second wall section 12b is permeable to the passage of fluid in at least a portion and it is substantially impermeable to the passage of other ingredients contained in delivery system 10.

Wall sections 12a and 12b optionally comprise a plasticizer that imparts flexibility and workability to the wall. Wall 12, comprising sections 12a and 12b, is nontoxic and, in a preferred embodiment, it maintains its physical and chemical integrity; that is, wall 12 does not erode during the dispensing period.

Compartment 18 comprises a beneficial agent 7 formulation, which beneficial agent 7 formulation comprises a beneficial agent 7, identified by dots, and a pharmaceutically acceptable carrier 21, identified by wavy lines. The pharmaceutically acceptable carrier may include more than one ingredient, such as a buffer 22, identified by horizontal dashes; a pharmaceutically acceptable vehicle 23, identified by vertical lines; a pharmaceutically acceptable surfactant 24, identified by slanted lines; and other formulation ingredients, as are known in the art.

Compartment 18 further comprises an expandable means or expandable driving member 25 optionally comprising members 25a–f. Expandable driving member 25 optionally comprises an osmagent homogeneously or heterogeneously blended with binder to form expandable driving member 25.

Compartment 18 may optionally comprise a partition layer 27. Partition layer 27 may optionally include, as in this embodiment, a piston 29, discussed in more detail with respect to FIG. 5. The partition layer 27 may include a portion which may be positioned between the drive piston 29 and the expandable driving member 25. The partition layer may comprise a composition that is substantially impermeable to the passage of fluid, and it further may act as a seal and restrict the passage of fluid present in the expandable driving member into the beneficial agent 7 formulation. Piston 29, alone or in cooperation with other portions of the partition layer 27, operate to essentially maintain the integrity of the beneficial agent 7 layer and the driving member layer 25. Portions of the partition layer 27 acts also to insure that the expanding driving force generated by the expandable driving member 25 is applied directly against piston 29 and thus is exerted on the formulation in compartment 18.

In operation, as the expandable member 25 absorbs and imbibes fluid through fluid-permeable second wall section 12b from the environment of use, it expands and pushes against piston 29 causing piston 29 to slide inside compartment 18. The piston may be lubricated, for example, using a silicone lubricant having the same characteristics as DOW 360 medical fluid 1000 cs. Piston 29 moves towards exit passageway 13, driving the beneficial agent 7 formulation in chamber 18 through passageway 13 for delivering the beneficial agent 7 to the environment of use. Second wall section 12b is telescopically capped by the engaging first wall section 12a. The two sections can be joined together by adhesive bond or various techniques such as solvent weld, thermal weld, ultrasonic weld, spin weld, induction weld, mechanical lock or by similar welding or bonding operations which may also be used in appropriate cases.

Delivery device 10 in FIG. 1 further comprises lead end 9, rear end 8, internal compartment 18, beneficial agent 7, pharmaceutically acceptable carrier 21, pharmaceutically acceptable buffer 22, pharmaceutically acceptable vehicle 23, and a pharmaceutically acceptable surfactant 24. In addition, a salt such as NaCl or KCl may be present in amounts of 1–4% by weight to assist stabilizing the state of formulation.

In a presently preferred embodiment, delivery device 10 comprises a plurality of expandable driving members 25a–f initially housed in second wall section 12b. This configuration is merely illustrative and there may be any number of driving member present. Generally, there are from one to six expandable driving members, this number is not controlling. The expandable driving members in a presently preferred embodiment are formed as depots or layers and comprise like or unlike compositions. For example, driving members 25a–f can be made as tablets comprising like osmopolymers or like osmagents, or they can comprise unlike osmopolymers or unlike osmagents, or one or more of the members can be a composition comprising an osmopolymer together with an osmagent. The members can be the same or they can be different.

Referring again to FIG. 1, end cap 38 further comprises a depot 122 in fluid communication between internal chamber 18 and exit passageway 13. Depot 122 can receive a material which is discharged, leached or eroded away during use. Preferably the material is wax or another material which can be discharged and depot 122 is sized to provide for sufficient pressure to discharge the material through passageway 13. This material serves several purposes: it seals delivery device 10 to prevent premature delivery of a beneficial agent 7 from delivery device 10 and to prevent evaporation of carrier components such as water during storage, it helps maintain the clean or optionally sterile environment inside delivery device 10, and it protects the ingredients inside the delivery device from oxidation by air and also protects the beneficial agent 7 from dilution by body fluids following implantation. More particularly, the seal 30 consistently releases at the same pressure using a 145 A wax in an end cap construction as described elsewhere in this application. In one preferred embodiment, the seal 30 releases at a pressure greater than 5–10 psi, more preferably greater than about 9 psi.

First wall section 12a, which surrounds the internal space of compartment 18 initially occupied by the beneficial agent 7 formulation, comprises a composition that does not adversely affect the beneficial agent 7, the osmopolymer, the osmagent, other ingredients in device 10, the host, or the like. First wall section 12a comprises a composition comprising means that substantially limits or prevents the passage of an external fluid into device 10. The phrase, "substantially limits or prevents," as used herein, indicates the volume of external fluid passing through first wall section 12a is substantially negligible, that is, about zero up to about 1 μl per day (see example 2 discussed more fully elsewhere in this application). Typical compositions for forming first section 12a are discussed in U.S. Patent Nos. 5,057,318 for example.

The second wall section 12b comprises a composition comprising means that aid in controlling fluid flux into the compartment area occupied by the expandable driving member 25. The composition is semipermeable; that is, it is permeable to the passage of external fluids such as water and biological fluids and it is substantially impermeable to the passage of beneficial agents, osmopolymers, osmagents, and the like. Typical compositions comprising semipermeable materials for forming wall 12b are known in the art, a non inclusive list includes the group consisting of a cellulose ester, a cellulose ether and a cellulose ester-ether, including, for example, cellulose acetate butyrate. These cellulosic polymers have a degree of substitution, D. S., on the anhydroglucose unit from greater than 0 up to 3, inclusive. By "degree of substitution" or "D. S." is meant the average number of hydroxyl groups originally present on the anhydroglucose unit comprising the cellulose polymer that are replaced by a substituting group. Representative fluid-permeable materials are discussed in U.S. Pat. Nos. 4,874,388, 5,034,229, and 5,057,318, for example. The amount of semipermeable materials presently preferred in wall 12b is from about 20% to 100%. In the presently preferred form, the wall is formed of polypropylene equivalent to medical grade polypropylene PD626 sold by Himont, because of its excellent low water transport qualities and the relative low surface tension relative to the beneficial agent 7 formulation as compared to other polycarbonates, especially when the beneficial agent is bovine somatotropin.

Representative materials that can be used to regulate further the fluid flux of wall 12b include materials that decrease the fluid flux and materials that increase the fluid flux of wall 12b. Representative materials optionally added to wall 12b for either decreasing or increasing the flux are presented in U.S. Pat. No. 5,034,229 and 5,135,523.

First wall section 12a and second wall section 12b optionally comprise a nontoxic plasticizer. Representative plasticizers suitable for forming wall 12a or wall 12b are well known in the art and examples are presented in U.S. Pat. No. 5,034,229 and 5,135,123.

Delivery device 10 in its compartment 18 can also comprise pharmaceutical carrier 21. Carrier 21 may optionally include viscosity modulating vehicles (23), buffers (22), surfactants (24), dyes, and other additives known in the art, examples of which are disclosed in U.S. Pat. No. 5,034,229 and 5,135,123 to comprise the beneficial agent 7 formulation.

In a presently preferred embodiment, the beneficial agent 7 is bovine somatotropin, in an amount of from about 25% to about 60% by weight (wt %) of the beneficial agent 7 formulation, preferably from about 30 wt % to about 45 wt %.

The expandable driving means 25 initially surrounded by second wall section 12b and operable for pushing the beneficial agent 7 composition 20 from delivery device 10 comprises, in a presently preferred embodiment, an osmopolymer. The osmopolymers interact with water and aqueous biological fluids and swell or expand to an equilibrium state. The osmopolymers exhibit the ability to swell in water and to retain a significant portion of the imbibed and absorbed water within the polymer structure. The expandable driving member 25 in another preferred embodiment comprises an osmagent. The osmagents are known also as osmotically effective solutes and they are also known as osmotically effective compounds. The osmotically effective compounds that can be used for the purpose of this invention include inorganic and organic compounds that exhibit an osmotic pressure gradient across a semipermeable, i.e. a fluid permeable, wall. The expandable driving member 25 yet in another preferred embodiment comprises an optional osmagent dispersed within the osmopolymer. The osmagent or osmopolymer can comprise a tablet or a layer or can be pressed into second wall section 12b. The osmagent or osmopolymer can be in any suitable form such as particles, crystals, pellets, granules, and the like, when pressed into a tablet layer and into wall section 12b. Osmagents and osmopolymers are known to the art in U.S. Pat. Nos. 3,865,108, 4,002,173, 4,207,893, 4,327,725, 4,612,008, 5,034,229, and 5,135,123 for example.

Piston 29, positioned between the beneficial agent composition and the expandable driving member 25, is a means for maintaining the separate identity of the beneficial agent composition and the driving member, for transmitting the force generated by the driving member against the beneficial agent composition, and for substantially restricting the passage of fluid between the beneficial agent composition and the driving member.

End cap 38, illustrated in FIG. I, provides a means for simply and conveniently assembling the device of the invention, and particularly for filling the device with internal components such as the driving members, the partition and the beneficial agent formulation. The end cap 38 is impermeable to fluid, providing protection for the fluid-sensitive beneficial agent. Materials for forming end cap 38 may be chosen from those materials useful in preparing impermeable first wall section 12a.

The terms "exit means" and "exit passageway", as used herein, comprise means and methods suitable for the metered release of the beneficial agent 7 from compartment 18 of delivery device 10. This includes maintaining sufficient efflux or outward velocity of the beneficial agent to prevent an inward flow of fluid from the external environment to dilute the beneficial agent formulation in the portion of the compartment comprised by the first wall section. The exit passageway 13 includes at least one passageway, orifice, or the like, through first wall section 12a for communicating with compartment 18. The expression "at least one passageway" includes aperture, orifice, bore, pore, porous element through which the agent can migrate, hollow fiber, capillary tube, porous overlay, porous insert, and the like. The expression also includes material that gets discharged, erodes or is leached from the wall in the fluid environment of use to produce at least one passageway in delivery device 10. The expression includes structural characteristics that concentrate stress at a precise point in the wall so that only a small amount of force will induce breakage in the wall, yielding a passageway through the wall from compartment 18 to the outside of the device. A passageway or passageways can be formed by the discharge, as a result of the pressure created by the expandable member for example, of a material such as a wax. The passageway can have any shape such as round, triangular, square, elliptical, and the like, for assisting in the metered release of beneficial agent from delivery device 10. Delivery device 10 can be constructed with one or more passageways in spaced-apart relations or more than a single surface of a dosage form. Passageways and materials, equipment and methods for forming passageways are disclosed in U.S. Pat. No. 5,034,229.

Delivery device 10 can be manufactured by standard manufacturing techniques. In one process, the first wall section 12a and the second wall section 12b are independently injection molded or extruded into the desired shape. Then, the first wall section 12a is filled with the beneficial agent composition. The second wall section 12b is filled with an expandable driving member or members, and the piston 29 is next added thereto in layered arrangement. Optionally, the piston 29 may be added to the first wall section 12a after filling the wall section with beneficial agent, in addition to, or instead of, the partition layer added to second wall section 12b. Next, the two sections at their open ends are slid together.

The delivery device of the present invention can be manufactured for delivering numerous beneficial agents, including drugs, at a controlled rate to a presently preferred biological environment of use such as warm-blooded animals, including humans; ruminants, such as bovines and sheep; porcines, such as hogs and swine; horses; and the like. The delivery devices provide for high loading of a beneficial agent and for its improved delivery in beneficially effective amounts (that is, amounts that provide a beneficial effect) over time. It is to be understood that the delivery devices can take a wide variety of shapes, sizes and forms adapted for delivering beneficial agents to environments of use. For example, the devices manufactured as delivery devices can be used for dispensing a beneficial agent in the anal-rectal passageway, in the cervical canal, as an artificial gland, in the vagina, as a subcutaneous or intraperitoneal implant, and the like. The delivery devices can be used in hospitals, nursing homes, outpatient clinics, sickrooms, veterinary clinics, farms, zoos, and other environments of use.

DETAILED DESCRIPTION OF EXAMPLES

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

A delivery device manufactured in the shape of an implantable delivery device according to the present invention is manufactured as follows.

An expandable driving member was prepared by first adding 10 liters of water and 526 g of polyvinylpyrrolidone to a stainless steel container and mixing the components for 1 hr to obtain a smooth binder solution. Next, approximately 20 kg of sodium chloride was milled in a mill to a number 21 size mesh screen. Then, 17.5 kg of the milled sodium chloride and 7.5 kg of sodium Carbomer®, a sodium salt of a polyacrylic polymer, were transferred to the granulator bowl of a fluid bed granulator and 2.46 kg of binder solution was slowly sprayed onto the materials in the granulator. Granules were formed in this manner. Next, the granulated material was sized by forcing it through a 0.0469 in mesh screen in a screen separator. Then, the granulation was divided into two 12.8 kg sub-batches. For each sub-batch, 130 g of magnesium stearate was added and the ingredients were blended for 3 min at 9 rpm to produce a homogeneous expandable driving composition. The composition next was pressed into osmotically active tablets in a tablet press at a pressure of 2,000 lbs to produce a round, flat-faced 266 mg tablet as an expandable driving member.

The semipermeable wall (membrane cup) that surrounds a compartment for containing the osmotically active tablets was prepared as follows. First, 1.0 kg of tributyl citrate and 9.0 kg of cellulose acetate butyrate were dry mixed in a mixer for 30 min. This produced a polymer/plasticizer blend of 90/10 ratio for the rate-controlling semipermeable second wall section 12b. The blend was then injection molded into a semi-permeable membrane cup of the desired shape with an open end for receiving an expandable driving member and for mating with the forward wall section, whose preparation is as follows.

The impermeable first wall section 12a of the delivery device 10 which forms the compartment holding the beneficial agent 7, is prepared by blending the polypropylene (Himont PD626) with a blue colorant (0.1% FD & C blue lake). The mixture is then injection molded into the first or forward impermeable wall section 12a in the desired shape, with the open second end 34 for mating with the semi-permeable second wall section or membrane cup 12b and an open forward or lead end 32 for the end cap 38. That portion of the first wall section 12a which mates with the semi-permeable second wall section or membrane cup 12b is molded with a diamond shaped pattern over a portion of its surface to enhance the adhesive bond between it and the membrane cup. Surface preparation ensures satisfactory adhesive bonding of polypropylene to other materials. In the case of the first wall section 12a, in addition to the mechanical configuration described above, this may be accomplished by either applying a primer to the glue-joint area or by treating the surface with a plasma made from a mixture of oxygen and tetrafluromethane gases prior to applying the adhesive. That mating portion of the first or forward wall section which mates with the end cap 38 is molded with circumferential, rectangular-shaped mortise 102 to facilitate ultrasonically welding the end cap 38 to the forward wall section 12a as described more fully elsewhere in this application.

The end cap 38 was prepared by blending polypropylene (Himont PD626) with a blue or white colorant (0.1% FD & C blue lake or 1.0% titanium dioxide, respectively). This mixture is then injection molded to form the end cap 38, as described more fully earlier in this application, having the exit aperture with a 0.017 inch diameter approximately 0.1 inches long, an internal cavity for containing a wax sealant material, and a precisely determined circumferential configuration around the outer perimeter of the end cap 38 to facilitate ultrasonic welding of the cap to the forward wall section 12a. This configuration includes a wedge shaped energy director with an included angle of 56°, which is beneficial to achieving a high quality ultrasonic weld with crystalline, polymeric materials being joined. The internal cavity is filled with molten wax (Witco 145), which solidifies to form a seal to the orifice port.

The piston 29 is prepared by insert injection molding Monsanto brand thermoplastic elastomer sold under the brand name "Santoprene® 271-55", into the piston with a circumferential, cantilevered lip at each end and a metal detection core in its center. The metal core is cylindrical in shape with a flat face at each end and is manufactured in a separate process by sintering at 1300° F. a metal alloy consisting of nickel and iron in a 50/50 ratio. The metal core is inserted into the mold when it is in the open position, and the thermoplastic elastomer is injected around it during the injection molding process. The piston 29 thus formed is lubricated with silicone medical fluid to facilitate movement of the piston inside the device during assembly and operation and to minimize piston set during storage.

The delivery device 10 is partially assembled by first charging the second wall section or semi-permeable membrane cup 12b with six of the osmotic tablets 25a-f. The second wall section 12b is then partially inserted into the impermeable first or forward wall section 12a of the device 10 and two drops of moisture-cured cyanoacrylate adhesive are dropped onto the exposed portion of the joint between the first and second wall sections, where the adhesive is drawn into the remainder of the joint by capillary action. The first and second wall sections 12 and 12b are then fully inserted to form a mechanically strong, water-tight seal. The lubricated piston 29 is then inserted through the remaining open end 32 of the first or forward wall section 12a, using a tool which allows air to pass by the piston 29 as it is moved into position against the osmotic tablets 25a-f and insert the piston within the wall section without having the skirt member rolled. The tool used is a thin-walled funnel open at both ends having an internal chamber for receipt of the piston therein.

Next, the delivery device subassembly, comprised of the second wall section or membrane cup 12b, the osmotic tablets 25a-f, the impermeable first or forward wall section 12a and the piston 29, is filled with 2250 mg of the beneficial agent 7 formulation at 35° C. The formulation is comprised of 36.5%±1.5% Zn-bST in a phosphate buffer, glycerols, wetting agent, salt excipient blend where the w/w/w/w proportions of phosphate buffer, glycerol, Tween-80, and KCl are 48.38/48.38/0.24/3.0 respectively. The phosphate buffer is 60:40 monobasic:dibasic sodium phosphate, and the molarity is 0.45. Then, a waxed end cap 38 is place into position on the open lead end 9 of the first wall section 12a by ultrasonic welding. The filled implant 10 is heat treated after being placed into a sterile package, for example, by heating the about 40° C. for about 16 hours.

EXAMPLE 2

The pistons according to the invention were tested as follows:

A formulation of ZnbST in a phosphate/glycerol/Tween/NaCl excipient was prepared using titrated water ($^3H_2O$). The specific activity of the labelled water was 1.0 mCi/ml, and should be sufficient to provide a detection limit of 1 μgm of water. The formulation was loaded into 10 mm osmotic implants with two different piston designs (1.0×and 1.5×), and a third group that had the compartment surrounding the osmotic driving member prehydrated.

TABLE 1

| Pump configurations | | |
| --- | --- | --- |
| Group | Piston | Pre-hydration |
| 1 | 1.0x | no |
| 2 | 1.5x | no |
| 3 | 1.0x | yes |

The implants were sampled in duplicate for group 1, and triplicate for groups 2 and 3, at intervals of 0, 3, 6, 12 and 18 weeks. For measurement of total water transport to the osmotic driving members, e.g. salt tablets, of the internal chamber 18 surrounded by the semipermeable wall section 12b, the second wall section 12b was separated from the first wall section 12a and the end cut off. Salt tablets were expelled and dissolved in water. An aliquot of the solution was added to the liquid scintillation cocktail and counted by standard liquid scintillation counting techniques. Table 2 lists the individual measurements of the total water content.

TABLE 2

TRANSPORT OF WATER FROM THE FORMULATION COMPARTMENT TO THE ENGINE COMPARTMENT DURING STORAGE AT 4 C.

| Group/ Replicate | Week 0 | Week 3 | Week 6 | Week 12 | Week 18 |
|---|---|---|---|---|---|
| 1/1 | 12 | 37 | 75 | 7413* | 130 |
| 1/2 | 12 | 50 | 68 | 98 | 148 |
| 1/3 | — | — | — | — | 162 |
| 2/1 | 460* | 43 | 66 | 331* | 515* |
| 2/2 | 14 | 41 | 67 | 97 | 150 |
| 2/3 | 1209* | 45 | 235* | 102 | 146 |
| 3/1 | 4 | 56 | 82 | 114 | 189 |
| 3/2 | 101* | 46 | 65 | 711* | 230* |
| 3/3 | 5 | 51 | 76 | 112 | 139 |

*possible statistical outlier (greater than 3 standard deviations from mean excluding theses points).

Figure 8:
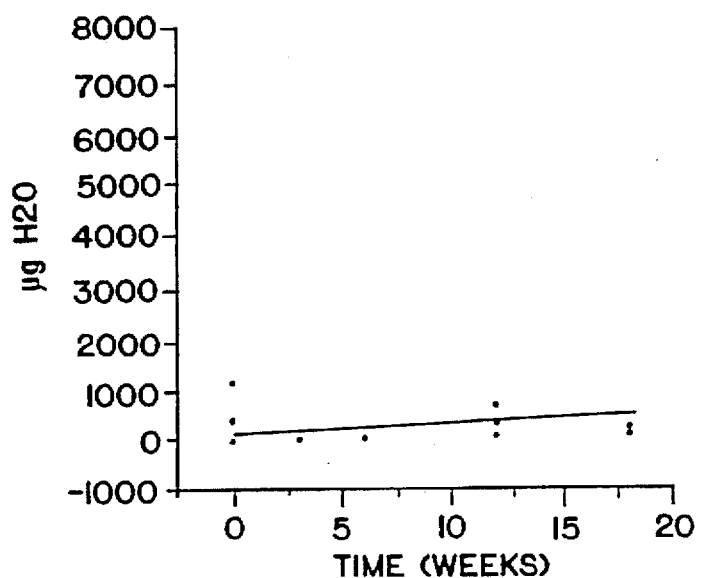
FIG. 8 is a graph showing the passage of water by the piston of FIG. 1 from the internal compartment surrounded by an impermeable first wall section into the internal compartment surrounded by permeable second wall section of FIG. 1.

FIG. 8 is a graph depicting the relationship between µgms of H$_2$O by-passing the piston versus time (weeks).

Figure 9:
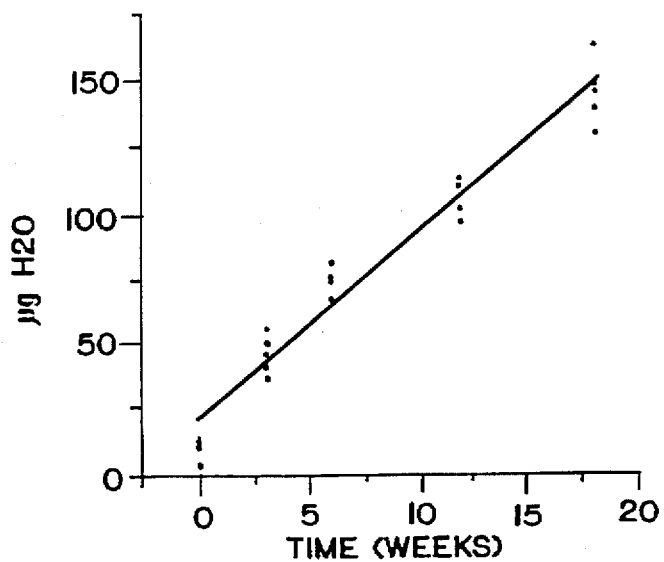
FIG. 9 is a graph showing the passage of water by the piston of FIG. 1 from the internal compartment surrounded by an impermeable first wall section into the internal compartment surrounded by permeable second wall section of FIG. 1, excluding data ≥ three standard deviations from the mean

FIG. 9 is a graph showing µgms of H$_2$O by-passing the piston versus time excluding outliers.

A variable amount of water ( 0.1–7 mg) transferred from the portion of the internal compartment 18 surrounded by the first wall section 12a to the portion surrounded by the second wall section 12b during the filling procedure for approximately 25% of the implants 10. There was a high pump to pump variability at all time points, on top of a small increase due to subsequent water transport from the internal compartment surrounded by the first wall section 12a to the salt tablets. The linear regression estimates of the rate of water transport along with 95% confidence intervals were as follows:

All data included: 20.0±8.9 µgms/week excluding outliers: 7.1±0.1 µg/week

Thus, the worst case estimate (upper 95% confidence interval with all data included) was 28.9 µgms per week, or approximately 1.5 milligrams per year. The best case estimate (lower confidence interval excluding outliers) was 7.0 µgms per week, or 0.36 milligrams per year. Therefore it was concluded, assuming the acceptable limit set by the amount of water that can be lost from the formulation without exceeding a 1% increase in protein assay, is approximately 60 milligrams, that the piston tested in these experiments was deemed adequate to maintain separation between the portion the internal compartment 18 surrounded by the first wall section 12a and the portion of the internal compartment 18 surrounded by the semipermeable second wall section 12b for the anticipated shelf life of five years or more, i.e., "substantially limits or prevents" the passage of fluid around the piston.

EXAMPLE 3

Delivery devices according to the present invention were tested in vivo as follows.

Example 3a (11466)

Weekly Subcutaneously Administered Pellets

A study was undertaken to determine the effect of 40 or 80 mg A-bST pellets administered subcutaneously weekly during a 84-day beef cattle study on 1) growth, 2) feed efficiency and 3) carcass composition.

One hundred eighty Angus X Hereford beef steers weighing approximately 350 kg (770 lbs) were used. Stocking density was 5 animals per pen. The trial consisted of 180 steers with replicates of 12 pens (60 animals) per treatment group (control, 40 mg bST/wk, and 80 mg bST/wk). The study lasted 84 days (12 weeks) exclusive of the pretreatment period. The diet for all animals, on a dry matter basis, contained 16% crude protein ("P"). Potable water was available ad libitum. Pens were randomly distributed among treatments:

TABLE 3

| Treatment | | | | |
|---|---|---|---|---|
| Trial | Group | Pens | Animals | Description |
| 1 | 1 | 12 | 60 | Control |
| 1 | 2 | 12 | 60 | 40 mg/wk A-bST Pellets |
| 1 | 3 | 12 | 60 | 80 mg/wk A-bST Pellets |

The animals were slaughtered for carcass analysis. The results are shown on the following Table:

TABLE 4

| Parameters | TREATMENT | | |
|---|---|---|---|
| | Control | 40 mg/wk bST Pellets | 80 mg/wk bST Pellets |
| Initial Body Wt (kg) | 390.3 | 390.3 | 390.3 |
| Final Body Wt (kg) | 499.5a | 495.0a | 510.4b |
| Carcass Wt. (kg) | 308.3 | 304.3 | 312.2 |
| Dressing Percent | 61.7 | 61.5 | 61.2 |
| Carcass Gain Response | — | No Gain | 39% |
| Non-Carcass Gain Response | — | No Gain | 61% | a, b - different superscripts indicate that numbers in a row are significantly different (p < .05)

It was observed that neither dressing percentage nor carcass weight were significantly increased. Further, at a higher dosage, most of the increase in body weight due to bST treatment was allocated to the non-carcass components.

Example 3b

Weekly Subcutaneous or Intraperitoneal Pellets

A study was undertaken to determine whether the effect of 80 mg A-bST pellets during an 84-day beef cattle study was comparable when administered subcutaneously and intraperitoneally.

Two hundred seventy Angus X Hereford beef steers weighing approximately 350 kg (770 lbs) were bought and divided into three study groups. Stocking density was 5 animals per pen. Each study group consisted of replicates of 6 pens (30 animals) per treatment group (control, 40 mgbST/wk subcutaneous pellet, and 80 mgbST/wk intraperitoneal pellet). The study lasted 84 days exclusive of the pretreatment period. The diet for all animals, on a dry matter basis, contained 16% crude protein. Potable water was available ad libitum. Pens were randomly distributed among the treatments:

TABLE 5

| Trial | Treatment | Pens | Animals | Description |
|---|---|---|---|---|
| 2 | 1 | 12 | 60 | Control |
| 2 | 2 | 12 | 60 | 80 mg/wk A-bST Subcutaneous (SQ) Pellet |
| 2 | 3 | 12 | 60 | 80 mg/wk A-bST Intraperitoneal (IP) Pellet |
| 3 | 1 | 12 | 60 | Control |
| 3 | 2 | 12 | 60 | 80 mg/wk bST SQ Pellet |
| 3 | 3 | 12 | 60 | 80 mg/wk bST IP Pellet |
| 4 | 1 | 12 | 60 | Control |
| 4 | 2 | 12 | 60 | 80 mg/wk A-bST SQ Pellet |
| 4 | 3 | 12 | 60 | 80 mg/wk A-bST IP Pellet |

The animals were slaughtered for carcass analysis. The results are shown in the following Tables:

TABLE 6

| Parameters | Control | TREATMENT 80 mg/wk SQ bST Pellets | 80 mg/wk IP bST Pellets |
|---|---|---|---|
| Carcass Wt. (kg) | 395.1 | 395.0 | 397.7 |
| Final Body Wt (kg) | 493.7a | 499.5a | 507.8a |
| Carcass Wt. (kg) | 304.2 | 304.2a | 311.2a |
| Dressing Percent (%) | 61.6a | 60.8b | 61.2ab |
| Carcass Gain (%) Response | — | 0% | 61% |
| Non-Carcass (%) Gain Response | — | 100% | 39% | a, b - different letters indicate that numbers in a row significantly different (p < .05)

It can be seen that, while the dressing percentage of subcutaneously-treated cattle was significantly decreased relative to the control, the dressing percentage of intraperitoneally-treated was not significantly changed relative to the control.

Example 3c

Combination of Intraperitoneal bST Osmotic Pump and Estrogen Pellets

A study was undertaken to determine whether the effects of intraperitoneal release of bST, of estrogen pellets, or of the combined effects of the two.

Two hundred fifty-six cross-bred large frame steers weighing approximately 430 kg (948 lb) were assigned to a control group and three treatment groups and implanted with intraperitoneal bST pumps or/and estrogen pellets. The bST formulation used was a 35% A bST load in a phosphate buffer, glycerol, Tween-80 and KCl excipient. The w/w/w % proportions respectively were 48.38/48.38/0.24/0%. The phosphate buffer was 60:40 monobasic:dibasic sodium phosphate at 1.0 M. The time of release of both bST and estrogen was 87 days prior to slaughter. The results are shown in the following Table.

TABLE 7

| Parameters | Control | TREATMENT 12 mg/d bST 0 Estrogen | 0 bST/200 ug/d Estrogen | 12 mg/d bST/200 ug/d Estrogen |
|---|---|---|---|---|
| Initial Body Wt (kg) | 430.3 | 430.3 | 430.3 | 430.3 |
| Final Body Wt (kg) | 544.9a | 552.2b | 567.1c | 576.4d |
| Carcass Wt (kg) | 334.2a | 340.3b | 349.3c | 359.7d |
| Dressing Percent (%) | 61.3a | 61.6a | 61.6a | 62.4b |
| Carcass Gain Response | N/A | 84% | 68% | 112% |
| Non Carcass Gain Response | N/A | 16% | 32% | −12% | a,b different superscripts indicate that number in a row are significantly different (P < .05)

These results indicated that a significant improvement in dressing percentage and carcass weight were achieved by intraperitoneal osmotic pump release of bST concurrent with estrogen treatment.

Example 3d

Combination of Intraperitoneal bST Osmotic Pump and Estrogen Pellet

A study was undertaken to determine performance of intraperitoneal osmotic pumps in finishing cattle concurrently being administered estrogen. Six hundred seventy-two cross-bred large frame cattle weighing approximately 412 kg were bought and assigned to a control group and six treatment groups of 96 cattle each. The cattle were implanted with intraperitoneal osmotic pumps capable of delivering 6, 12, 15 or 18 mg bST per day during an 84-day period ending with slaughter. The cattle received estrogen pellets during a 126-day period ending with slaughter. The estrogen release is estimated at about 200 ug/d. The results are shown in the following table.

TABLE 8

| load Parameters | Control | 30% 6 mg/d | 12 mg/d | 40% 15 mg/d | 45% 6 mg/d | 12 mg/d | 18 µg/d |
|---|---|---|---|---|---|---|---|
| Initial Body Wt (kg) | 411.9 | 411.9 | 411.9 | 411.9 | 411.9 | 411.9 | 411.9 |
| Final Body Wt (kg) | 555.1a | 565.6bc | 568.7bc | 569.6c | 561.8b | 563.5bc | 566.5bc |

TABLE 8-continued

| load Parameters | Control | 30% 6 mg/d | 12 mg/d | 40% 15 mg/d | 45% 6 mg/d | 12 mg/d | 18 µg/d |
|---|---|---|---|---|---|---|---|
| Carcass Wt (kg) | 343.0a | 353.1bc | 357.2d | 355.4cd | 350.8b | 351.3b | 353.8bcd |
| Dressing Percent | 61.8a | 62.4b | 62.8b | 62.4b | 62.4b | 62.4b | 62.5b |
| Carcass Response | — | 96% | 104% | 86% | 116% | 99% | 95% |
| Non-Carcass Response | — | 4% | −9% | 14% | −16% | 1% | 5% |

The results confirm that concurrent intraperitoneal treatment of finishing beef cattle with bST and estradiol significantly increase dressing percentage and carcass weight and furthermore allocated most of the increased weight to the carcass components,

EXAMPLE 4

Figure 10:
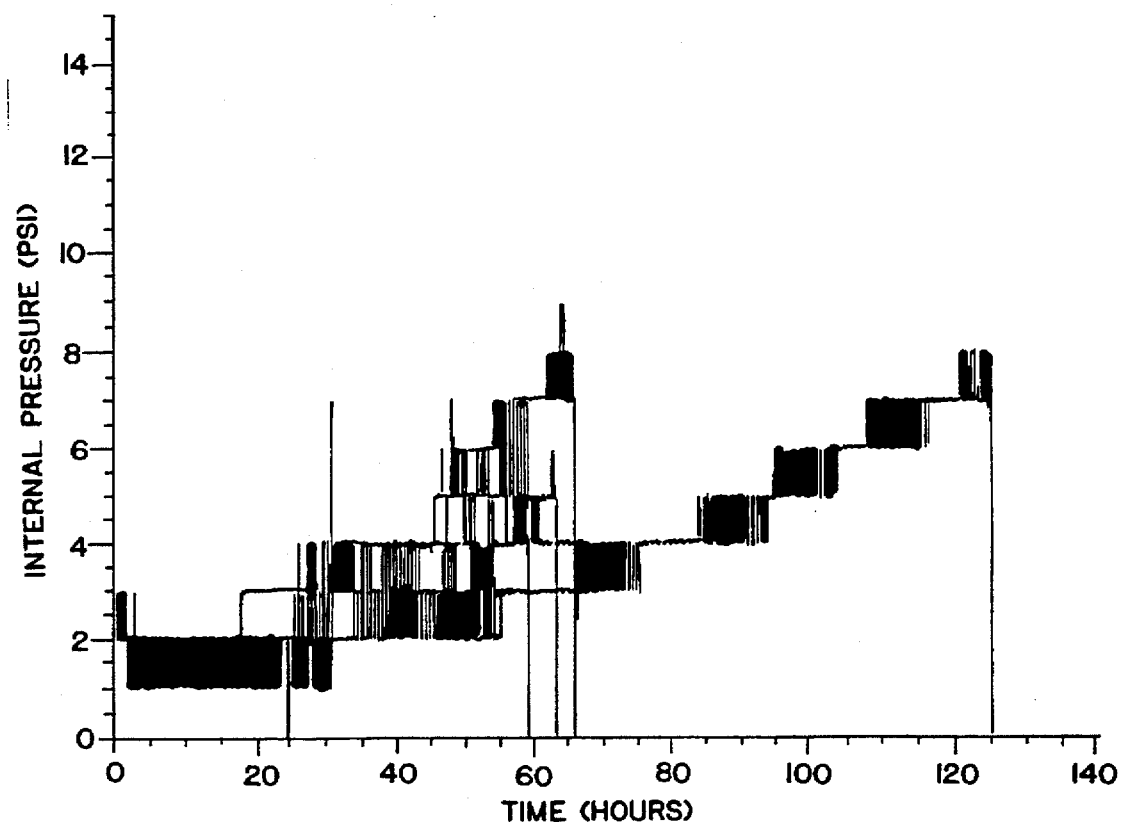
FIG. 10 is a graph showing the pressure requirement for seal release over time (hours).

FIG. 10 is a graph depicting the real time pressure release for a seal of Multiwax X-145 a wax having a thickness of 0.050 inches. The pressure at which the seals blew was between 6 and 9 psi from exit passageway of having a 0.017 diameter and a length of 0.100 inches.

Thus, an exit passage having a 0.017 inch diameter and a length of 0.100 inches, in fluid contact or abutted by a seal of 0.050 thick, would burst the seal between about 6–9 psi.

EXAMPLE 5

Figure 11:
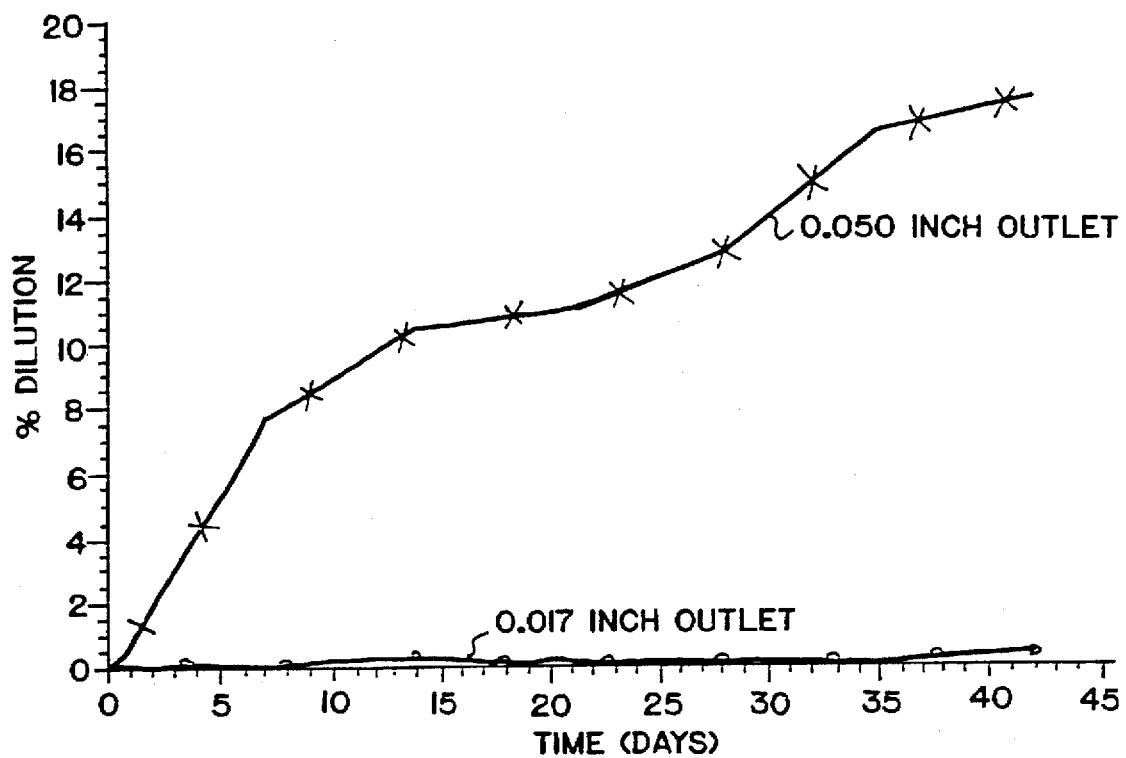
FIG. 11 is a graph showing the effect of exit aperture diameter on water diffusion.

FIG. 11 is a graph showing the effect of the exit port aperture diameter on the diffusion of water using an exit passageway length of 0.100 inches and specified diameter. Empirical observations of the respective devices indicate that the beneficial agent formulation turned white in all devices with 0.050 inch diameter outlets with small pockets of water entrained in the formulation. The beneficial agent formulation was clear in all devices having an exit port aperature of about 0.017 inches in diameter.

Thus an exit aperature having a diameter of 0.017 inches provides sufficient outward velocity or efflux of the beneficial agent from the compartment defined by the first wall section, i.e., "substantially limits or prevents" diffusion of fluid back into the internal compartment defined by the first wall section.

The novel devices of this invention use means for the obtainment of precise release rates in a fluid environment of use while simultaneously maintaining the integrity of the device and the stability of the fluid-sensitive beneficial agent 7 within the device. While there has been described and pointed out features of the invention as applied to presently preferred embodiments, those skilled in the art will appreciate that various modifications, changes, additions and omissions in the devices illustrated and described can be made without departing from the spirit of the invention.

What is claimed is:

1. In a delivery device for storing and protecting a beneficial agent formulation and for dispensing the beneficial agent formulation to an animal, the delivery device having a housing comprising a fluid impermeable portion and a fluid permeable portion forming an internal compartment;

a beneficial agent formulation in the internal compartment;

an expandable driver in the compartment for pushing the beneficial agent formulation from the delivery device;

a partition substantially impermeable to fluid, the partition disposed between the beneficial agent formulation and the expandable driver;

and exit passageway in the housing for delivering the beneficial agent formulation from the internal compartment to the animal over a prolonged period of time improvement comprising:

the partition including a body portion and a biased skirt for slidably engaging the housing portions, the biased skirt being biased radially outward from the body portion to slidably engage the housing, wherein the partition includes a conical skirt extending obliquely outward from the body portion to be biased radially outward from the body portion while slidably engaging with the housing.

2. A delivery device for storing and protecting a beneficial agent formulation and for dispensing the beneficial agent formulation to an animal, the delivery device having:

a housing comprising a fluid impermeable portion, and a fluid permeable portion, the portions forming an internal compartment;

a beneficial agent formulation in the internal compartment;

an expandable driver in the compartment for pushing the beneficial agent formulation from the delivery device;

a partition layer substantially impermeable to fluid between the beneficial agent formulation and the expandable driver, wherein the partition layer includes a body portion and biasing means for slidably engaging the first wall section, the body portion adapted to be slidably received within the first wall section and the biasing means having a portion separated from and overlapping the body portion to slidably engage the first wall section, wherein the biasing means includes a conical skirt extending obliquely outward from the body portion to be biased radially outward from the body portion while slidably engaging with the housing; and an exit passageway for delivering the beneficial agent formulation from the internal compartment to the animal over a prolonged period of time, the improvement comprising headspace spaced away from the exit passageway for accumulating an air volume within the portion of the internal compartment containing the beneficial agent formulation at a location away from the exit passageway.

3. A delivery device for storing and protecting a beneficial agent formulation and for dispensing the beneficial agent formulation to an animal, the delivery device having:

a housing comprising a fluid impermeable portion and a fluid permeable portion, the portions forming an internal compartment;

a beneficial agent formulation in the internal compartment;

an expandable driver in the compartment for pushing the beneficial agent formulation from the delivery device; and an exit passageway for delivering the beneficial agent formulation from the internal compartment to the animal over a prolonged period of time, the improvement comprising headspace for accumulating an air volume within the internal compartment, and further comprising a partition layer substantially impermeable to fluid between the beneficial agent formulation and the expandable means, wherein the partition layer includes a body portion and biasing means for slidably engaging the first wall section, the body portion adapted to be slidably received within the first wall section and the biasing means having a portion separated from and overlapping the body portion to slidably engage the first wall section, wherein the biasing means includes a conical skirt extending obliquely outward from the body portion to be biased radially outward from the body portion while slidably engaging with the housing, wherein the conical skirt separates from and overlaps the body portion while slidably engaging with the fluid impermeable portion.

4. A delivery device according to claim 3 wherein the fluid impermeable portion includes a first wall section and an end cap, the end cap comprising an inwardly extending portion, the inwardly extending portion and the first wall section defining the headspace, the headspace comprising an annular air receiving cavity therebetween.

5. A delivery device according to claim 4, further including means for maintaining a seal between the exterior environment and the interior compartment until the osmotic pressure within the device reaches a predetermined pressure of between greater than 5 and 10 psi.

6. A delivery device according to claim 4, wherein the end cap includes mating means for adapting the end cap to ultrasonic welding to the first wall section, the mating means positioned where the end cap and the first wall section join.

7. A delivery device as set forth in claim 6, wherein the end cap further comprises a first side and a second side, and wherein the mating means includes a tenon extending outwards from the second side of the end cap, the first wall section defining a mortise therein, the tenon sized and positioned for receipt within the mortise.

8. In a delivery device for storing and protecting a beneficial agent formulation and for dispensing the beneficial agent formulation to an animal, the delivery device having:

a housing comprising a fluid impermeable portion and a fluid permeable portion, the portions forming an internal compartment;

a beneficial agent formulation in the internal compartment;

an expandable driver in the compartment for pushing the beneficial agent formulation from the delivery device; and an exit passageway for delivering the beneficial agent formulation from the internal compartment to the animal over a prolonged period of time, the improvement comprising headspace for accumulating an air volume within the internal compartment, wherein the fluid impermeable portion comprises a first wall section, and the fluid permeable portion comprises a second wall section, a portion of the second wall sized to be telescopically received within a portion of the first wall section the wall sections defining an adhesive receiving space containing an adhesive therebetween.

9. A delivery device according to claim 8, wherein the wall sections comprise means for abutting with the first wall section and smoothing the transition from the first wall section to the second wall section.

10. In a delivery device for storing and protecting a beneficial agent formulation and for dispensing the beneficial agent formulation to an animal, the delivery device having:

a housing comprising a fluid impermeable wall section and a fluid permeable portion forming an internal compartment;

a joint for joining the fluid impermeable portion to the fluid permeable portion;

a beneficial agent formulation in the internal compartment;

expandable driver in the compartment adjacent the fluid permeable portion for pushing the beneficial agent formulation from the delivery device; and exit means in the fluid impermeable section for delivering the beneficial agent formulation from the delivery device to the animal over a prolonged period of time, the improvement comprising:

the fluid permeable portion and the fluid impermeable portion defining an adhesive receiving space containing an adhesive therebetween; and a joint for joining the fluid impermeable portion to the fluid permeable portion, the joint providing a smooth transition from the fluid impermeable portion to the fluid permeable portion.

11. A delivery device according to claim 10, wherein the joint includes a buttress formed upon the fluid permeable portion and positioned to abut the fluid impermeable portion.

12. A delivery device according to claim 10 which further comprises a partition layer substantially impermeable to fluid between the beneficial agent formulation and the expandable means, wherein the partition layer includes a body portion and biasing means for slidably engaging the first wall section, the body portion sized to be slidably received within the first wall section and the biasing means having a portion separated from and overlapping the body portion to slidably engage the first wall section.

13. A delivery device according to claim 10 which further comprises a piston separating the beneficial agent from the expandable driving means, wherein the piston includes a conical skid extending distally, obliquely outwardly from a body portion to separate from and overlap the body portion while slidably engage with the first wall section.

14. A delivery device for storing and protecting a beneficial agent formulation and for dispensing the beneficial agent formulation to an animal, the delivery device comprising:

a) a housing comprising a first wall section, a second wall section, and an end cap, the first wall section, the second wall section and the end cap assembled together to form an internal compartment, wherein the first wall section and the end cap are substantially impermeable to the passage of fluid and, wherein the second wall section is permeable in at least a portion to the passage of fluid;

b) means for abutting the first wall section with the second wall section;

c) a beneficial agent formulation in a portion of the internal compartment comprised by the first wall section and the end cap;

d) expandable means in a portion of the compartment comprised by the second wall section for pushing the beneficial agent formulation from the delivery device;

e) a partition layer substantially impermeable to fluid, the partition layer between the beneficial agent formulation and the expandable means, wherein the partition layer includes a body portion and a conical skirt extending obliquely outward from the body portion to be biased radially outward from the body portion while slidably engaging the first wall section; and f) exit means in the end cap for delivering the beneficial agent formulation from the delivery device to the animal.

15. A delivery device according to claim 14 wherein the end cap further comprises an inwardly extending portion, the inwardly extending portion and the first wall section defining a space therebetween.

16. A delivery device according to claim 14, wherein the end cap further includes mating means for adapting the end cap to ultrasonic welding to the first wall section, the mating means positioned where the end cap and the second wall section join.

17. A delivery device as set forth in claim 16, wherein the mating means includes a tenon extending outwards from the end cap, the second wall section defining a mortise therein, the tenon sized and positioned for receipt within the mortise.

18. A delivery device according to claim 14, wherein the means for abutting with the first wall section includes a buttress formed upon the second wall section and positioned to abut the first wall section.

* * * * *